US012806414B2

(12) United States Patent
Lee

(10) Patent No.: US 12,806,414 B2
(45) Date of Patent: Nov. 24, 2026

(54) SUCTION-TYPE COMPOSITE HANDPIECE AND BEAUTY DEVICE INCLUDING SAME

(71) Applicant: Dong Shin Lee, Hwaseong-si (KR)

(72) Inventor: Dong Shin Lee, Hwaseong-si (KR)

( * ) Notice: Subject to any disclaimer, the term of this patent is extended or adjusted under 35 U.S.C. 154(b) by 446 days.

(21) Appl. No.: 18/526,568

(22) Filed: Dec. 1, 2023

(65) Prior Publication Data

US 2024/0181252 A1 Jun. 6, 2024

(30) Foreign Application Priority Data

Dec. 2, 2022 (KR) ........................ 10-2022-0166497

(51) Int. Cl.
*A61N 1/32* (2006.01)
*A61H 9/00* (2006.01)
(Continued)

(52) U.S. Cl.
CPC ........... *A61N 1/328* (2013.01); *A61H 9/0057* (2013.01); *A61N 1/36003* (2013.01);
(Continued)

(58) Field of Classification Search
CPC ...... A61N 1/0452; A61N 1/0472; A61N 1/06; A61N 1/328; A61N 1/36003; A61N 1/36034; A61N 1/40; A61H 9/0057
See application file for complete search history.

(56) References Cited

U.S. PATENT DOCUMENTS 11,247,039 B2 * 2/2022 Schwarz .............. A61N 5/0616
11,464,993 B2 * 10/2022 Schwarz ................ A61N 1/403
(Continued)

FOREIGN PATENT DOCUMENTS

JP 2008-173232 A 7/2008
KR 10-2015-0002464 A 1/2015
(Continued)

OTHER PUBLICATIONS

The extended European search report dated Apr. 4, 2024 for corresponding European Patent Application No. 23213731.5 (7 pages).
(Continued)

*Primary Examiner* — Shaun R Hurley
(74) *Attorney, Agent, or Firm* — Hauptman Ham, LLP

(57) ABSTRACT

A beauty device includes a suction-type composite handpiece that can be fixed to the skin and can automatically massage the skin. The beauty device may include a main body and a plurality of suction-type composite handpieces. Each handpiece may include a suction part, a contact part, radio frequency (RF) terminals, electrical muscle stimulation (EMS) terminals, a temperature sensor, and a cooling part. The suction part may suck the skin to inside and massage the skin based on a suction pressure pattern. The contact part may protrude from a lower outer peripheral surface of the suction housing. The RF terminals may output RF energy. The EMS terminals may output EMS and cross between the RF terminals. The temperature sensor may detect a temperature of the skin sucked into the suction housing. The cooling part may be located inside the suction housing and lower the temperature of the sucked skin.

4 Claims, 4 Drawing Sheets

(51) Int. Cl.
*A61N 1/36* (2006.01)
*A61N 1/40* (2006.01)

(52) U.S. Cl.
CPC ........... *A61N 1/36034* (2017.08); *A61N 1/40* (2013.01); *A61H 2201/0214* (2013.01); *A61H 2201/10* (2013.01); *A61H 2201/5082* (2013.01)

(56) References Cited

U.S. PATENT DOCUMENTS

| | | | | |
|---|---|---|---|---|
| 11,491,329 | B2 * | 11/2022 | Schwarz | A61N 1/328 |
| 2009/0306647 | A1 | 12/2009 | Leyh et al. | |
| 2012/0271206 | A1 * | 10/2012 | Shalev | A61N 1/322<br>607/3 |
| 2021/0220210 | A1 * | 7/2021 | Berdahl | A61H 7/001 |
| 2022/0211997 | A1 | 7/2022 | Schwarz et al. | |
| 2022/0249836 | A1 | 8/2022 | Schwarz et al. | |
| 2022/0370814 | A1 * | 11/2022 | Epshtein | A61N 2/002 |

FOREIGN PATENT DOCUMENTS

| | | | |
|---|---|---|---|
| KR | 10-2019-0014888 | A | 2/2019 |
| KR | 10-2318658 | B1 | 10/2021 |
| KR | 10-2021-0130793 | A | 11/2021 |

OTHER PUBLICATIONS

Office Action dated Jun. 5, 2023 in Korean Application No. 10-2022-0166497.

* cited by examiner

SUCTION-TYPE COMPOSITE HANDPIECE AND BEAUTY DEVICE INCLUDING SAME

CROSS REFERENCE TO RELATED APPLICATION

The present application claims priority to Korean Patent Application No. KR 10-2022-0166497 filed Dec. 2, 2022, the entire contents of which are incorporated herein for all purposes by this reference.

BACKGROUND

Technical Field

The disclosure relates to a combination beauty device based on radio frequency (RF) and electrical muscle stimulation (EMS). In particular, the disclosure relates to a suction-type composite handpiece capable of automatically massaging the skin in a state of being fixed to the skin, and to a beauty device including the same.

Description of Related Technology

Recently, as interest in health and beauty has increased, procedures to remove fat are being performed to manage body shape. One of the fat removal procedures is a method of removing the fat layer by applying RF energy to the skin. As the RF energy penetrates deep into the skin and generates heat energy, it promotes collagen formation and induces the death of fat cells, enabling body management. Additionally, EMS treatment can send micro-currents to the skin to cause muscle contraction and relaxation, thereby strengthening muscles and promoting collagen formation.

SUMMARY

One aspect is a suction-type composite handpiece that can be fixed to the skin and can automatically massage the skin, and a beauty device including the same.

Another aspect is a suction-type composite handpiece that can prevent the risk of burns during RF procedures, and a beauty device including the same.

Another aspect is a suction-type composite handpiece that can maximize the efficiency of RF and EMS procedures, and a beauty device including the same.

Another aspect is a beauty device that may include a plurality of suction-type composite handpieces and a main body. The plurality of suction-type composite handpieces output radio frequency (RF) energy and electrical muscle stimulation (EMS) and are fixed to a skin even when held no hand by sucking the skin. The main body is connected to the plurality of suction-type composite handpieces. Also, the main body adjusts pressure and time for the plurality of suction-type composite handpieces to suck the skin based on a predetermined suction pressure pattern, and controls operations of the plurality of suction-type composite handpieces.

In certain embodiments, each of the plurality of suction-type composite handpieces may include a suction part, a contact part, a plurality of RF terminals, a plurality of EMS terminals, a temperature sensor, and a cooling part. The suction part may have a suction housing for sucking the skin to inside and massaging the skin based on the suction pressure pattern. The contact part may protrude from a lower outer peripheral surface of the suction housing, and have an edge connected to the suction housing and formed as a curved surface. The plurality of RF terminals may output RF energy and be formed along an edge where an inner surface of the suction housing and a lower surface of the contact part meet, thus preventing RF energy concentration. The plurality of EMS terminals may output EMS and be arranged to cross between the plurality of RF terminals. The temperature sensor may be located inside the suction housing and detect a temperature of the skin sucked into the suction housing. The cooling part may be located inside the suction housing and lower the temperature of the skin sucked into the suction housing.

In certain embodiments, the main body may control the plurality of suction-type composite handpieces to output the RF energy and the EMS alternately or simultaneously based on a predetermined pattern without interfering with each other.

In certain embodiments, the plurality of suction-type composite handpieces may be arranged in series on the skin to generate a beat effect between the EMSs output respectively from the handpieces.

In certain embodiments, the suction housing may have a square pyramid shape with curved edges and a rectangular bottom, and the contact part may have a rectangular ring shape.

In certain embodiments, the RF terminals may be arranged to face or be adjacent to each other.

In certain embodiments, the EMS terminals may be arranged to face or be adjacent to each other, and each of the EMS terminals may be formed in an arch shape.

According to embodiments of the disclosure, the suction-type composite handpiece of the beauty device can be fixed to the skin by sucking the skin and can massage the skin using a predetermined suction pressure pattern.

In addition, the suction-type composite handpiece of the beauty device can prevent the risk of burns during RF treatment by including the temperature sensor and the cooling part.

Further, the suction-type composite handpieces of the beauty device can maximize the efficiency of EMS treatment by creating a beat effect between EMSs when used in series.

DETAILED DESCRIPTION

Figure 1:
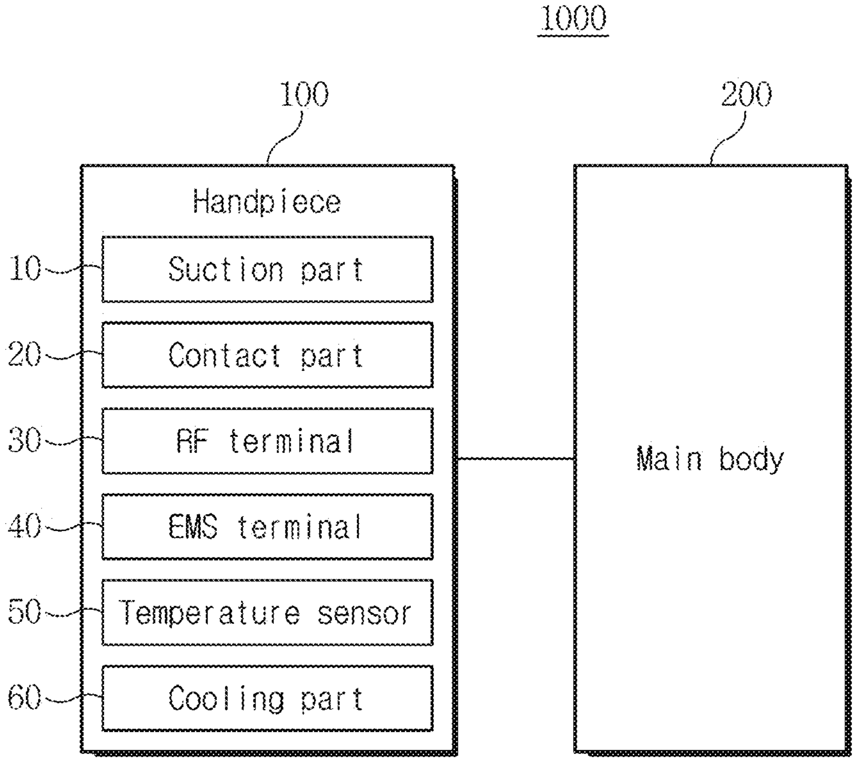
FIG. 1 is a block diagram showing a beauty device according to the disclosure.

There is a beauty device in which an RF terminal and an EMS terminal are formed in one handpiece and can be used simultaneously or alternately. However, this beauty device has limitations in the size of each terminal and the distance between terminals, which reduce the efficiency of the procedure.

Additionally, in the case of typical RF procedures, if the RF handpiece stays in one area for more than 5 seconds, there is a risk of burns due to heat accumulation on the skin. Therefore, there is the inconvenience of the operator having to continuously check the temperature and rub the skin. In addition, the subcutaneous fat melted through RF treatment must be discharged through blood vessels or lymph to achieve the effect of fat removal, so a typical RF device has the inconvenience of requiring the operator to massage separately.

Hereinafter, various embodiments of the disclosure will be described in detail with reference to the accompanying drawings. The disclosure may, however, be embodied in many different forms and should not be construed as being limited to the embodiments set forth herein. Rather, these embodiments are provided so that the disclosure will be thorough and complete and will fully convey the scope of the disclosure to those skilled in the art.

In the following description of embodiments, techniques that are well known in the art and not directly related to the disclosure are not described. This is to clearly convey the subject matter of the disclosure by omitting an unnecessary explanation. In the disclosure, the same or corresponding elements are denoted by the same reference numerals.

FIG. 1 is a block diagram showing a beauty device 1000 according to the disclosure.

Referring to FIG. 1, the beauty device 1000 includes a suction-type composite handpiece 100 and a main body 200. The handpiece 100 outputs radio frequency (RF) energy and electrical muscle stimulation (EMS). The main body 200 is connected to the handpiece 100. The main body 200 controls the operation of the handpiece 100 such as adjusting the pressure and time for the handpiece 100 to suck the skin based on a predetermined pattern.

The main body 200 is capable of controlling the overall operation of the handpiece 100. For example, the main body 200 can adjust the pressure and time for the handpiece 100 to suck the skin, and can control the pattern in which the handpiece 100 outputs RF energy and EMS. In addition, the main body 200 may be provided with a holder for holding the handpiece 100 on the outside, and may include a touch screen for receiving control commands from the user and displaying the operating status.

Hereinafter, the suction-type composite handpiece 100 according to the disclosure will be described in more detail.

Figure 2:
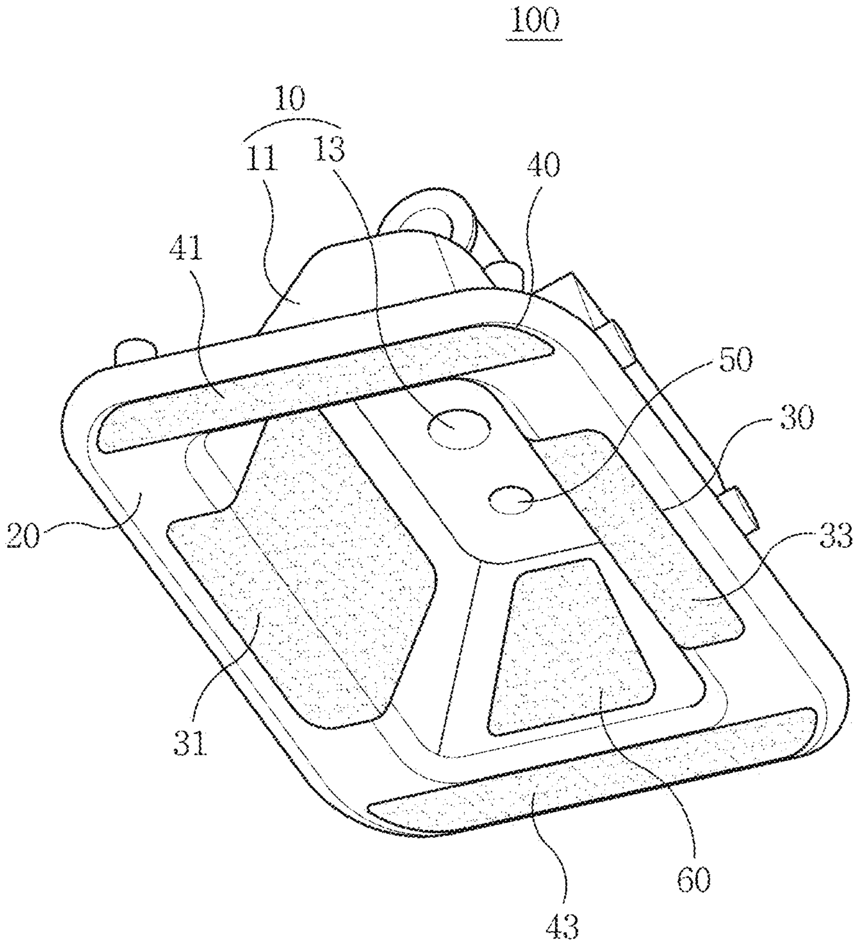
FIG. 2 is a perspective view showing a suction-type composite handpiece according to the disclosure.

FIG. 2 is a perspective view showing a suction-type composite handpiece 100 according to the disclosure.

Referring to FIGS. 1 and 2, the suction-type composite handpiece 100 includes a suction part 10, a contact part 20, a plurality of RF terminals 30, a plurality of EMS terminals 40, a temperature sensor 50, and a cooling part 60.

The suction part 10 has a suction housing 11 that sucks the skin to the inside and is thereby fixed to the skin. The contact part 20 protrudes from the lower outer peripheral surface of the suction housing 11. The plurality of RF terminals 30 output RF energy, and the plurality of EMS terminals 40 output EMS. The temperature sensor 50 is located inside the suction housing 11 and detects the temperature of the skin sucked into the suction housing 11. The cooling part 60 is located inside the suction housing 11 and lowers the temperature of the skin sucked into the suction housing 11.

As shown, the suction housing 11 may have a square pyramid shape with curved edges and a rectangular bottom. However, the shape of the suction housing 11 is not limited to the illustrated example, and may be a hemisphere shape, a polygonal dome shape, etc. If a space is created between the suction housing 11 and the skin when the skin is sucked into the suction housing 11, RF energy is concentrated only on the portion in contact with the RF terminal 30, which may cause burns to the skin. To prevent this, the inside of the suction housing 11 may be curved to minimize the space between the suction housing 11 and the skin. A suction hole 13 connected to a suction pump (not shown) of the main body 200 may be formed in the upper center of the suction housing 11.

Therefore, the suction-type composite handpiece 100 can be fixed to the skin by sucking the skin even if not continuously held by the operator, and can massage the skin by a predetermined suction pressure pattern.

As described above, the temperature sensor 50 is located inside the suction housing 11 and can detect the temperature of the skin sucked into the suction housing 11. If the detected temperature of the skin sucked into the suction housing 11 exceeds a predetermined temperature, the cooling part 60 can cool the skin.

Therefore, the suction-type composite handpiece 100 can eliminate the inconvenience of the operator having to frequently check the skin temperature with a thermometer, and thus prevent the risk of burns during RF treatment.

The contact part 20 protrudes from the lower outer peripheral surface of the suction housing 11, and its edge connected to the suction housing 11 may be formed as a curved surface. The shape of the contact part 20 varies depending on the shape of the suction housing 11. Therefore, if the suction housing 11 has the shape of a square pyramid with a rectangular bottom, the contact part 20 may have a rectangular ring shape. However, the shape of the contact part 20 is not limited to this and may be a circular ring, a polygonal ring, etc.

The RF terminal 30 may be formed along an edge where the inner surface of the suction housing 11 and the lower surface of the contact part 20 meet. For example, the RF terminal 30 may be formed in an L shape. Such a shape of the RF terminal 30 can increase the cross-sectional area where the RF terminal 30 touches the skin, thus preventing energy concentration.

The RF terminals 30 may be arranged to face or be adjacent to each other. For example, when the contact part 20 is in the form of a rectangular ring, there may be first and second RF terminals 31 and 33 formed to face each other on the long sides of the rectangular ring.

A typical monopolar RF scheme can deliver energy deep into the skin, but there is a problem in that it requires a separate plate in addition to an RF handpiece. In addition, a typical bipolar RF scheme is convenient for treatment because it uses only an RF handpiece without a plate, but there is a problem in that it is difficult to deliver energy deep into the skin.

On the other hand, since the suction-type composite handpiece 100 according to the disclosure can generate heat in the skin sucked between the first and second RF terminals 31 and 33 formed to face each other, it can transfer energy deep to the skin without a separate plate, allow a target point to be clearly set, and allow a target temperature to be reached quickly.

The EMS terminals 40 may be arranged to face or be adjacent to each other. For example, when the contact part 20 is in the form of a rectangular ring, there may be first and second EMS terminals 41 and 43 formed to face each other on the short sides of the rectangular ring. Since the EMS terminal 40 is formed on the short side of the rectangular ring, the size of the EMS terminal 40 becomes smaller compared to the RF terminal 30 formed on the long side of the rectangular ring. Accordingly, by forming the EMS terminal 40 in an arch shape extending from the short side of the rectangular ring to both corners as shown, the area where the EMS terminal 40 touches the skin can be maximized.

The suction-type composite handpiece 100 can output RF energy and EMS alternately or simultaneously.

Figure 3:
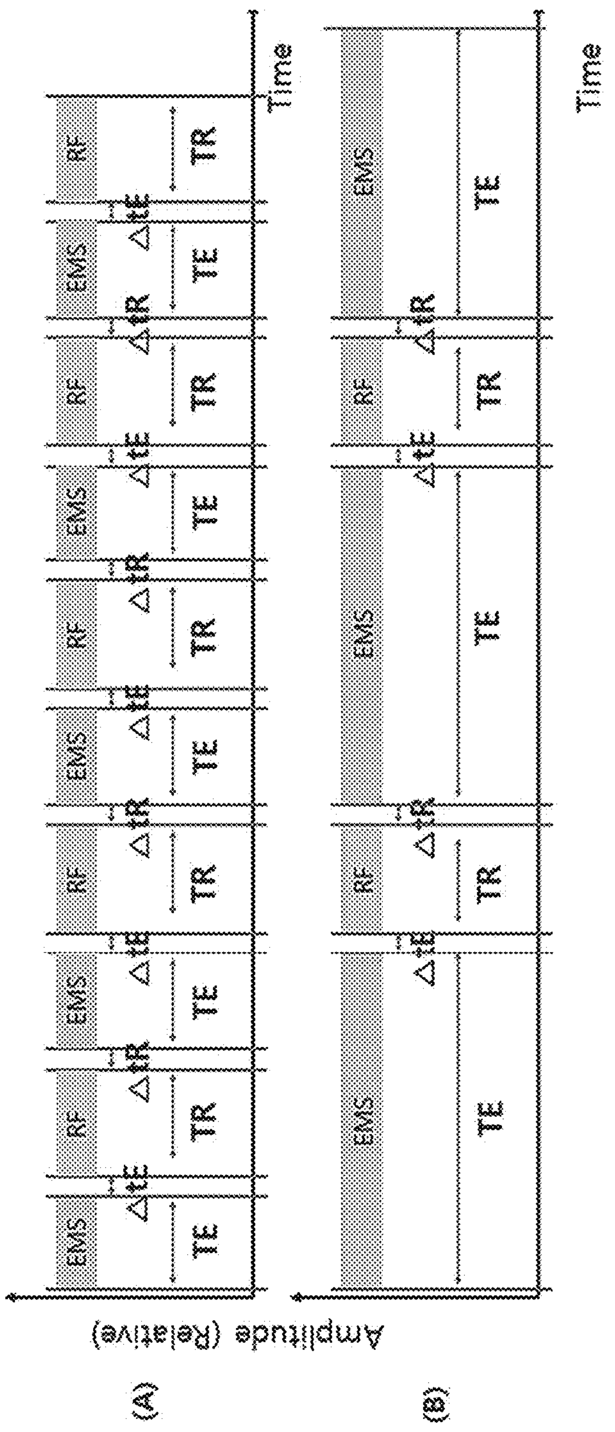
FIG. 3 is a graph showing the amplitude of radio frequency energy and EMS alternately output from a suction-type composite handpiece according to the disclosure.

FIG. 3 is a graph showing the amplitude of radio frequency energy and EMS alternately output from a suction-type composite handpiece 100 according to the disclosure.

Referring to FIG. 3, TE denotes the time during EMS is output, and TR denotes the time during RF energy is output. In addition, ΔtE denotes the time from when the output of EMS ends to when the output of RF energy begins, and ΔtR denotes the time from when the output of RF energy ends to the time when the output of EMS begins.

In FIG. 3, graph A shows the amplitude when RF energy and EMS are output alternately but TE and TR are the same, and graph B shows the amplitude when RF energy and EMS are output alternately but TE and TR are different. According to graphs A and B, it can be seen that when RF energy and EMS are output alternately, the RF energy and the EMS do not interfere with each other regardless of TE and TR. Therefore, the handpiece 100 according to the disclosure can stably output RF energy and EMS.

Meanwhile, the beauty device 1000 may include a plurality of suction-type composite handpieces 100.

Figure 4:
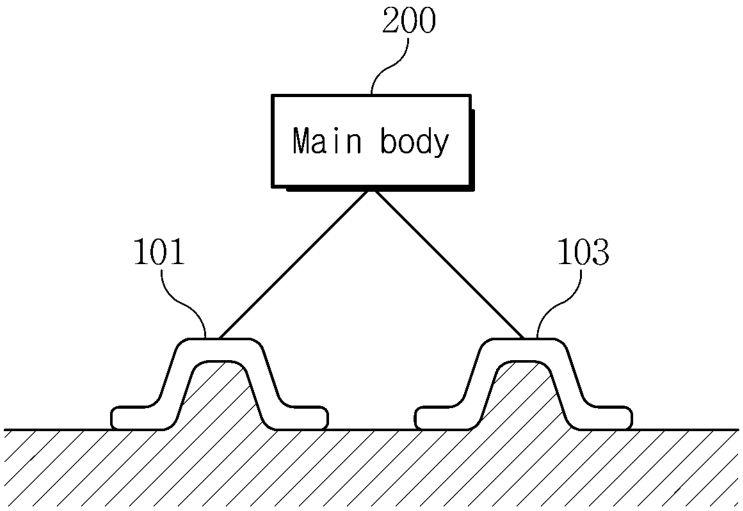
FIG. 4 is a view showing an example of the use of a beauty device including a plurality of suction-type composite handpieces according to the disclosure.

FIG. 4 is a view showing an example of the use of a beauty device including a plurality of suction-type composite handpieces according to the disclosure.

Referring to FIG. 4, the beauty device according to the disclosure may include a plurality of handpieces 101 and 103. In this case, each handpiece is connected to the same main body.

In the case of using a plurality of handpieces 101 and 103 arranged in series on the skin, a beat effect occurs between EMSs output respectively from the handpieces 101 and 103. In this case, the area and depth through which EMS flows to the skin may increase compared to the case of using a single handpiece. This beat effect increases as the number of handpieces, that is, the number of EMS terminals increases. Accordingly, the beauty device according to the disclosure can overcome the limitations of the relatively small area of the EMS terminal and maximize the efficiency of EMS treatment.

While the disclosure has been particularly shown and described with reference to exemplary embodiments thereof, it will be understood by those skilled in the art that various changes in form and details may be made therein without departing from the scope of the disclosure as defined by the appended claims.

What is claimed is:

1. A beauty device comprising:

a plurality of suction-type composite handpieces each of which is configured to output radio frequency (RF) energy and electrical muscle stimulation (EMS) and to suck a skin so as to be fixed without being held by a hand; and a main body connected to the plurality of suction-type composite handpieces, the main body configured to:

adjust pressure and time for the plurality of suction-type composite handpieces to suck the skin based on a predetermined suction pressure pattern, and control operations of the plurality of suction-type composite handpieces, wherein each of the plurality of suction-type composite handpieces includes:

a suction part having a suction housing configured to suck the skin to inside and massage the skin based on the suction pressure pattern;

a contact part protruding from a lower outer peripheral surface of the suction housing, and having an edge connected to the suction housing and formed as a curved surface;

a plurality of RF terminals configured to output RF energy and formed along an edge where an inner surface of the suction housing and a lower surface of the contact part meet, thus preventing RF energy concentration;

a plurality of EMS terminals configured to output EMS, wherein each of the plurality of the EMS terminals is arranged between two of the plurality of RF terminals;

a temperature sensor located inside the suction housing and configured to detect a temperature of the skin sucked into the suction housing; and a cooling part located inside the suction housing and configured to lower the temperature of the skin sucked into the suction housing, wherein the main body is configured to control the plurality of suction-type composite handpieces to output the RF energy and the EMS alternately or simultaneously based on a predetermined pattern without interfering with each other, and wherein the plurality of suction-type composite handpieces are arranged in series on the skin to generate a beat effect between the EMSs output respectively from the handpieces.

2. The beauty device claim 1, wherein the suction housing has a square pyramid shape with curved edges and a rectangular bottom, and the contact part has a rectangular ring shape.

3. The beauty device claim 2, wherein the RF terminals are arranged to face or be adjacent to each other.

4. The beauty device claim 2, wherein the EMS terminals are arranged to face or be adjacent to each other, and wherein each of the EMS terminals is formed in an arch shape.

* * * * *